(12) United States Patent
Bonlie

(10) Patent No.: US 6,210,317 B1
(45) Date of Patent: Apr. 3, 2001

(54) TREATMENT USING ORIENTED UNIDIRECTIONAL DC MAGNETIC FIELD

(76) Inventor: Dean R. Bonlie, #109, 5421 11 Street N.E., Calgary, Alberta (CA), T2E 6M4

(*) Notice: Subject to any disclaimer, the term of this patent is extended or adjusted under 35 U.S.C. 154(b) by 0 days.

(21) Appl. No.: 09/115,330

(22) Filed: Jul. 14, 1998

(51) Int. Cl.[7] .............................. A61B 17/52; A61N 2/00
(52) U.S. Cl. ................................................................ 600/9
(58) Field of Search ................................ 600/9, 14, 15, 600/13

(56) References Cited

U.S. PATENT DOCUMENTS 5,817,000 * 10/1998 Souder ................................... 600/15

* cited by examiner

Primary Examiner—Cary O'Connor
Assistant Examiner—Brian Szmal
(74) Attorney, Agent, or Firm—Pillsbury Winthrop LLP

(57) ABSTRACT

A method of treating a patient who lives in a relatively weak magnetic field such as is naturally present by using an oriented, unidirectional, DC magnetic field. The magnetic field is aligned to pass through the patient's body in substantially the same direction that the Earth's magnetic field did during the majority of recent cell division within the patient's body. The first step of the present invention is to determine what the orientation of the Earth's magnetic field has been with respect to the patient's body during cell division in the recent past. The next step is to position the patient's body within a treating magnetic field. The magnetic field is oriented to correspond to some extent to the direction of the Earth's magnetic field determined in the first step. The magnetic field is constrained to prevent fringing magnetic fields from passing through any part of the patient's body in an obtuse direction with respect to the direction of the Earth's magnetic field determined in the first step. The treating magnetic field has zero frequency and is at least 500 gauss in intensity at its weakest point within the portion of the patient's body to be treated.

18 Claims, 5 Drawing Sheets

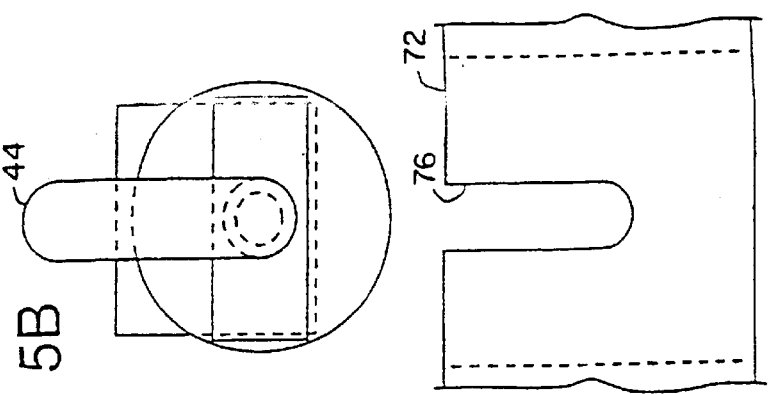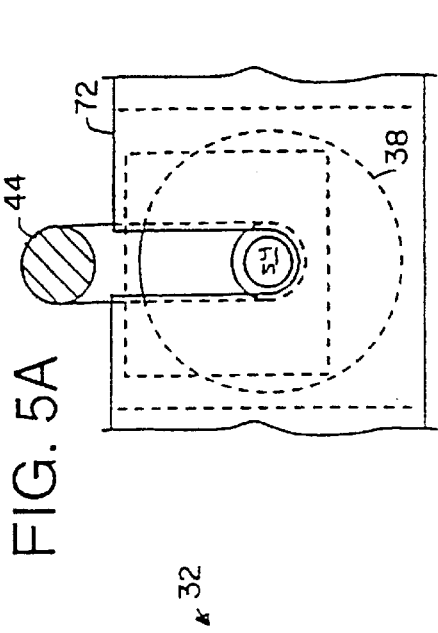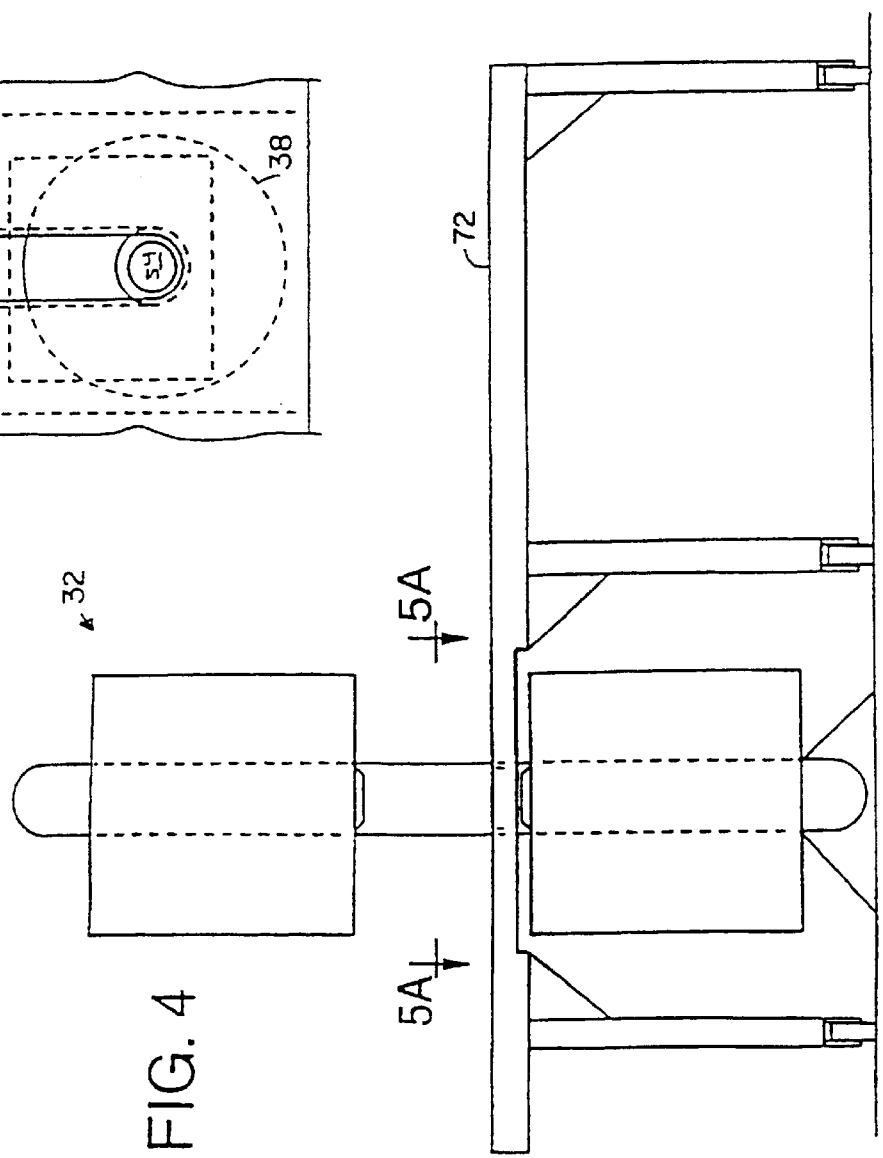

TREATMENT USING ORIENTED UNIDIRECTIONAL DC MAGNETIC FIELD

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE INVENTION

1. Field of the Invention

The invention relates generally to the treatment of disease using magnetic fields, and more specifically, to the treatment of degenerated tissue and bones using relatively high-magnitude, zero frequency, magnetic fields of the proper orientation.

2. Description of the Related Art Including Information Disclosed Under 37 CFR 1.97 and 1.98

Others have attempted to use magnetic fields or waves in the treatment of human diseases. A non-exhaustive list of references to such treatment includes:

Smith U.S. Pat. No. 96,044
Slater et al. U.S. Pat. No. 561,448
Bachelet U.S. Pat. No. 849,653
Hahnemann U.S. Pat. No. 2,161,292
Manning U.S. Pat. No. 3,893,462
Brus et al. U.S. Pat. No. 4,481,091
Castel U.S. Pat. No. 4,587,957
Liboff et al. U.S. Pat. No. 5,087,336
Liboff et al. U.S. Pat. No. 5,183,456
Liboff et al. U.S. Pat. No. 5,211,622

Various people have used magnetic fields of specific low frequencies in an attempt to stimulate specific substances that have matching resonant frequencies. Unfortunately, as the substances become excited, their resonant frequencies shift, ending the effect of the magnetic field.

To counter this effect, others have used a variety of magnetic frequencies, sweeping through the range, or used impulses of magnetic fields. None, however have achieved any substantial success in rejuvenating damaged or diseased tissue.

What is needed, then, is an effective method for treating disease using magnetic fields.

BRIEF SUMMARY OF THE INVENTION

The present invention pertains to a method of treating a patient who lives in a relatively weak magnetic field such as is naturally present through the use of a high-intensity "treating" magnetic field.

The treating magnetic field must be aligned to pass through the patient's body in substantially the same direction that the Earth's magnetic field did during the majority of recent cell division within the patient's body. As such, the first step of the present invention is to determine what the orientation of the Earth's magnetic field has been with respect to the patient's body during cell division in the recent past.

The next step of the present invention is to position the portion of the patient's body to be treated within a relatively high-intensity magnetic field. The treating magnetic field preferably is oriented to correspond to some extent to the direction of the Earth's magnetic field determined in the first step. At a minimum, the treating magnetic field must be oriented such that it is within 90 degrees of the Earth's magnetic field determined in the first step. An angle greater than 90 degrees would result in a component of the treating magnetic field being antiparallel to the direction of the Earth's magnetic field determined in the first step.

As a feature of the present invention, the treating magnetic field is constrained such that any fringing or "return" magnetic fields do not pass through any part of the patient's body in an obtuse direction with respect to the direction of the Earth's magnetic field determined in the first step.

As another feature of the present invention, the treating magnetic field has zero frequency, that is, it is a "DC" magnetic field having no frequency modulation.

As yet another feature of the present invention, the treating magnetic field is at least 500 gauss in intensity. Higher field intensities are possible and may be used to good effect. In a preferred embodiment of the present invention, a treating magnetic field intensity of at least 2000 gauss is used. Good results have been achieved using a treating magnetic field intensity of 20,000 gauss.

These and other features, advantages, and objects of the present invention will become apparent to those skilled in the art upon examination of the following specification when taken in conjunction with the drawings.

BRIEF DESCRIPTION OF THE SEVERAL VIEWS OF THE DRAWING

FIG. 4 is an elevation view of a horizontal patient support and the magnetic field generator of FIG. 2.

FIG. 5A is a sectional view of a portion of the patient support of FIG. 4 with the magnetic field generator in a treating position, taken along line 5A—5A of FIG. 4.

FIG. 5B is a plan view of portion of the patient support shown in FIG. 5A with the magnetic field generator separated from the patient support.

DETAILED DESCRIPTION OF THE INVENTION

Method of Present Invention

Figure 1:
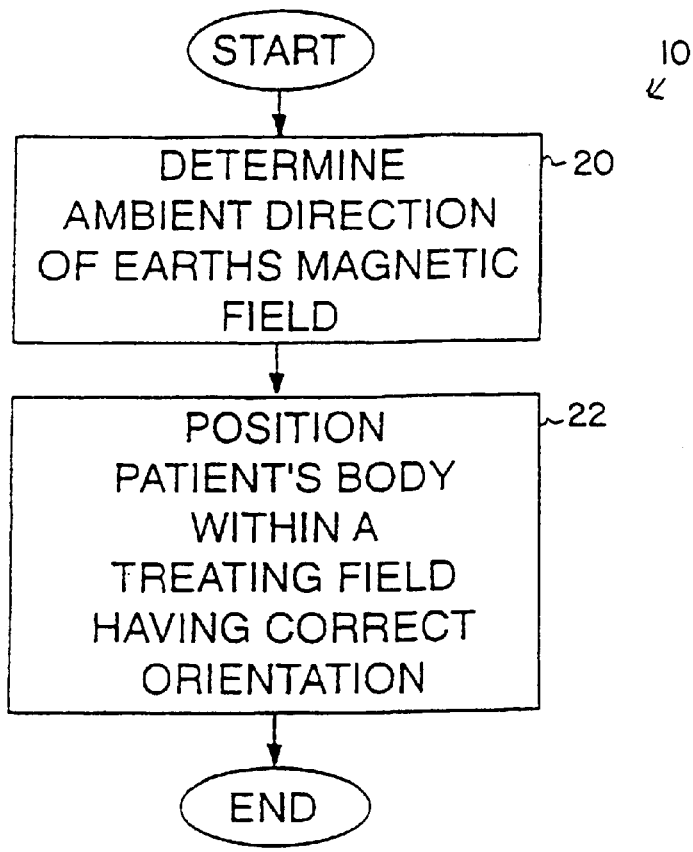
FIG. 1 is a block diagram of a method of treating a patient according to the present invention.

Referring first to FIG. 1, the present invention pertains to a method 10 of treating a portion of a patient's body using a relatively high-intensity magnetic field. During treatment, the treating magnetic field must be aligned to pass through the patient's body in substantially the same direction that the Earth's magnetic field did during the majority of recent cell division within the patient's body. Therefore, as shown in FIG. 1, the first step 20 of the present invention is to determine the predominate direction of the Earth's magnetic field as it passed through the patient's body during the majority of its cell division in the recent past. Determining that direction is simplified because approximately 70 percent of a body's cell division occurs within its first two hours of sleep. Thus, by knowing where on Earth and in what position a patient sleeps, the direction of the Earth's magnetic field with respect to the patient can be determined. Although the Earth's magnetic field has various orientations with respect to a person throughout the day as the person moves, for convenience, the term "ambient direction" shall mean herein the direction that the Earth's magnetic field passes through a person's body during its first two hours of sleep.

For example, a person who sleeps in a supine position in the Northern hemisphere experiences an ambient direction of the Earth's magnetic field that is substantially antiparallel to that magnetic field experienced by another person who sleeps in a prone position in the Northern hemisphere. Likewise, a person who sleeps in a supine position in the Northern hemisphere experiences the same ambient direction of the Earth's magnetic field as another person who sleeps in a prone position in the Southern hemisphere. The ambient direction of the Earth's magnetic field also can be determined for a person who sleeps consistently on a particular side.

This first step 20 of determining the ambient direction of the Earth's magnetic field is more problematic for a patient who does not sleep in a consistent position. In such a case, there is no orientation for which a majority of recent cell division has occurred. If time permits, such a person could be directed to attempt to sleep in a consistent position for a sufficient number of months before attempting treatment according to the present invention.

It should be recognized that different portions of a patient's body may have different orientations, or inconsistent orientations, depending on the patient's sleep patterns. For example, a patient's limbs and head are more likely to change position throughout the first two hours of sleep even while the patient's trunk remains still.

It also should be recognized that a patient may not have an accurate perception of his or her sleeping position during the first two hours of sleep. Patients may be observed for a period of time before commencing treatment to verify a person's predominate sleeping position.

The second step 22 of the present invention is to position the portion of the patient's body to be treated within a treating magnetic field.

The treating magnetic field must meet a number of criteria. First, the direction of the treating magnetic field must be within 90 degrees of the ambient direction determined in the first step. An obtuse angle would result in a component of the treating magnetic field being antiparallel to the ambient direction. Preferably, the treating magnetic field corresponds more closely, or is even parallel, to the ambient direction.

Second, the treating magnetic field must be properly constrained such that any fringe or "return" magnetic fields do not pass through any part of the patient's body in an undesirable direction. This "nonreversing" constraint can be accomplished either by using magnets that have such large surface areas that the entire body of the patient fits between them in a substantially unidirectional magnetic field or by providing a return path for the magnetic field by way of a magnetic circuit.

Third, the treating magnetic field must have zero frequency, that is, be a "DC" magnetic field with no modulation. It should not have frequency components or be pulsed.

Fourth, the treating magnetic field must have sufficient intensity, being at least 500 gauss. Preferably, the magnetic field intensity is even higher, being at least 2000 gauss. Experiments have been done with good results using magnetic field intensities of 20,000 gauss.

Apparatus for Implementing the Present Invention

The treating magnetic field required in the second step 20 of the method 10 of the present invention can be provided using many different devices without deviating from the principles of the invention. For example, either permanent magnets or electromagnets can be used to provide a magnetic field of sufficient field intensity. Likewise, different arrangements of a single magnet or multiple magnets and associated magnetic circuitry for return magnetic fields may be used to ensure that reversing fields do not pass through a patient's body. Additionally, either the magnets, the patient support, or both the magnets and the patient support, may be adjusted to ensure that the treating magnetic field passes through a patient's body with the correct orientation.

Figure 2:
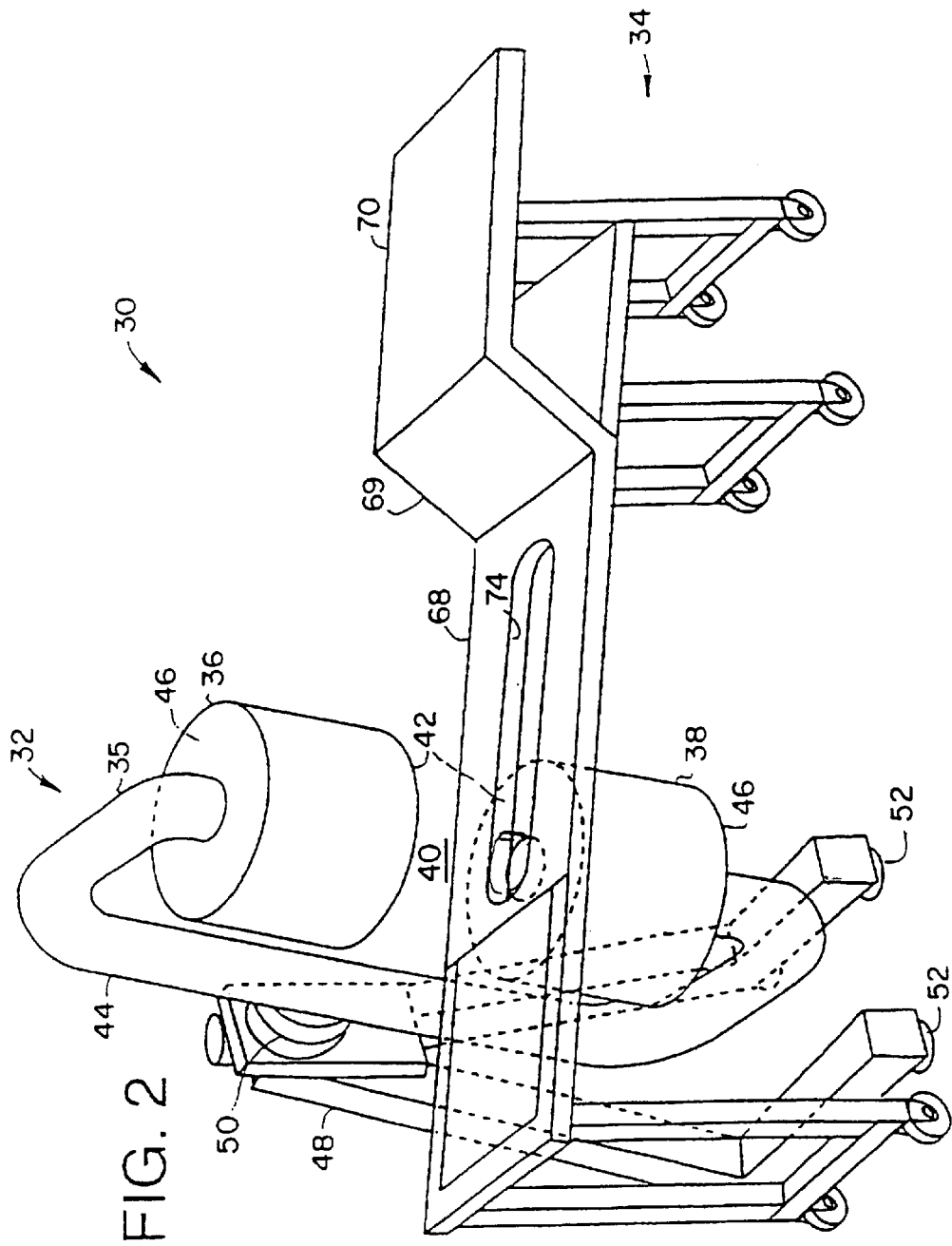
FIG. 2 is a perspective view of a device using two electromagnets for generating an oriented, unidirectional, DC magnetic field to treat a patient according to the present invention.

Referring now to the drawings and with particular reference to FIG. 2, an apparatus 30 for practicing the present invention is shown. The apparatus 30 consists of two major elements: a magnetic field generator 32 for producing a treating magnetic field and a patient support 34 for positioning a patient within the treating magnetic field.

The magnetic field generator 32 shown in FIG. 2 comprises a magnetic circuit 35 having an upper electromagnet 36 and a lower electromagnet 38 separated by a gap 40 on their adjacent pole faces 42 and connected by a C-shaped core 44 (or "C-core") on their opposing poles 46. The C-core 44 provides a return path for the magnetic field and completes the magnetic circuit 35. The C-core 44 must be of sufficient size and magnetic capacity such that virtually all of the return magnetic field flows through the C-core 44. Any return magnetic field that does not pass through the C-core 44 likely will pass through a portion of a patient's body in a direction that does not correspond to a correct orientation. In the embodiment shown in FIG. 2, the C-core 44 has a circular cross section with an 8 inch (20.3 cm) diameter.

The magnetic circuit 35 is supported by an A-frame type support structure 48 that provides stability and mobility for the magnetic circuit 35. A pivoting joint 50 permits the magnetic circuit 35 to be rotated about a horizontal axis, allowing the magnetic circuit 35 to be used with patient supports having different configurations. The connection between the support structure 48 and the C-core 44 may also allow for raising and lower the C-core 44. The support structure 48 also includes a plurality of wheels 52 to facilitate moving the magnetic circuit 35.

Figure 3:
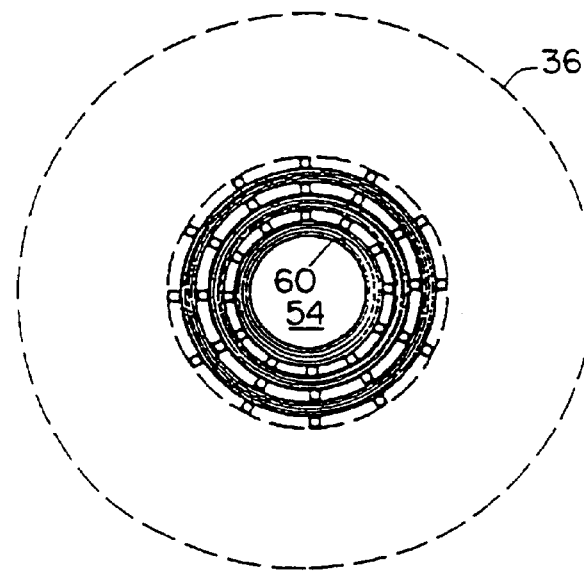
FIG. 3 is a simplified sectional view of an electromagnet, taken along line 3—3 of FIG. 2.

Referring now to FIG. 3, the two electromagnets 36, 38 are wrapped on a solid core 54. The core 54 is from 4 to 10 inches (from 10.16 to 25.4 cm) in diameter, with the larger diameters being preferred. The core 54 may be constructed to be integral with the C-core 44. The core 54 may be made from a magnetic material such as soft annealed steel. Laminated transformer core material may also be used. However, a laminated core material is not necessary because the electromagnets 36, 38 used for implementing the present invention do not use alternating magnetic fields.

Each electromagnet 36, 38 comprises more than 9,000 windings of copper wire and is wrapped to a length of 24 inches (60.96 cm) along the length of the core 54 and a diameter of 26 inches (66.0 cm).

The electromagnets 36, 38 are wired in parallel with a power supply (not shown) to create magnetic fields of the same sense. For example, the positive pole of the upper electromagnet 36 would face the negative pole of the lower electromagnet 38. Similarly, by reversing the direction of current within the electromagnets 36, 38, the negative pole of the upper magnet 36 would face the positive pole of the lower electromagnet 38.

As shown in FIG. 3, a cross section of the upper electromagnet 36 shows the core 54 wrapped with the first three groups of layers of windings. The first group of layers 60 of windings is wrapped directly around the core 54. The first group 54 of windings is wrapped to a thickness of approximately 0.75 inches (1.905 cm). Next, a plurality of longitudinal spacer strips 62 are distributed around the windings. The spacer strips 62 must be constructed of a nonmagnetic, heat resistant material and have sufficient length to cover the preceding adjacent windings. The spacer strips 62 provide a passageway approximately 0.25 inches (0.635 cm) thick through which a coolant may pass through. After the spacer strips 62 are in place, a second group of layers of windings is wrapped over the spacer strips 62. Multiple alternating layers of windings and spacers make up the upper electromagnet 36. The lower electromagnet 38 is constructed in a similar manner.

The spacer strips 62 provide an unobstructed pathway for cooling air to pass through the electromagnet 36 in a longitudinal direction parallel to the center core 54. To provide better cooling, the cooling air can be refrigerated and forced through the electromagnets 36, 38 with ducting.

It should be recognized by those skilled in the art that coolants other than refrigerated air can be used. Liquids such as water or nonconductive oils can be used. Furthermore, the electromagnets 36, 38 could by cryogenically cooled with liquid hydrogen, helium, nitrogen, or liquid air.

Referring again to FIG. 2, the patient support 34 shown is designed for a patient to lie on in a supine position. The patient lies back against a platform 68 while a raised section 70 supports the patient's lower legs in a comfortable position. Sections 69 and 70 are adjustable to raise the patient's legs higher or lower.

The raised section 70 can be moved longitudinally along the platform 68 to position the portion of the patient's body to be treated within the gap 40.

The patient support 34 is ergonomically designed to keep a patient comfortable during the long treatment times. The platform 68 has a slight incline to elevate a patient's head; in the embodiment shown in FIG. 2 the incline is 22.5 degrees. The raised section 70 is also inclined at the same angle. The short section 69 that connects the platform 68 and the raised section 70 forms an angle of 122 degrees with the platform 68.

The core of the lower electromagnet 38 preferably extends upward beyond the windings of the electromagnet to virtually flush with the upper surface of the platform 68. A longitudinal slot 74 in the platform facilitates the movement of the magnetic field generator 32 along the platform 68. In the embodiment shown in FIG. 2, the longitudinal slot 74 is 4 inches (10.16 cm) wide. Cores wider than the width of the slot 74 must taper down to fit in the slot 74.

This extension of the core of the lower electromagnet 38 decreases the width of the gap, thereby minimizing any fringing magnetic fields which could pass through a patient in a non-complementary direction.

The patient support 34 of FIG. 2 is designed primarily for those patients who sleep in either a supine or prone position. As discussed above, a positive or negative magnetic field can be generated by reversing the direction of current through the upper and lower electromagnets 36, 38. Referring now to FIG. 4, a horizontal patient support 72 also can be used in the method 10 of the present invention. The horizontal patient support 72 provides more options for positioning of the patient, similar to the patient's bed at home. Thus, the horizontal patient 72 support allows the patient to lie in a prone or supine position during treatment. The horizontal patient support 72 also allows the patient to lie on his or her side, allowing treatment according to the present invention of those who sleep on their sides.

Referring now to FIGS. 5A and 5B, a transverse slot 76 in the horizontal patient support 72 facilitates easy passage of the extended core 54 of the lower electromagnet 38 to the center of the horizontal patient support 72.

It will be recognized that a patient support that forces a patient to lie in a supine or prone position can be used to treat patients who sleep on their sides. In such a situation, the magnetic field generator 32 must be able to be rotated such that the upper electromagnet 36 and the lower electromagnet 38 are at the same elevation. Furthermore, the C-core 44 must be able to be rotated such that the patient can lie between the electromagnets 36, 38 without interference.

Figure 6:
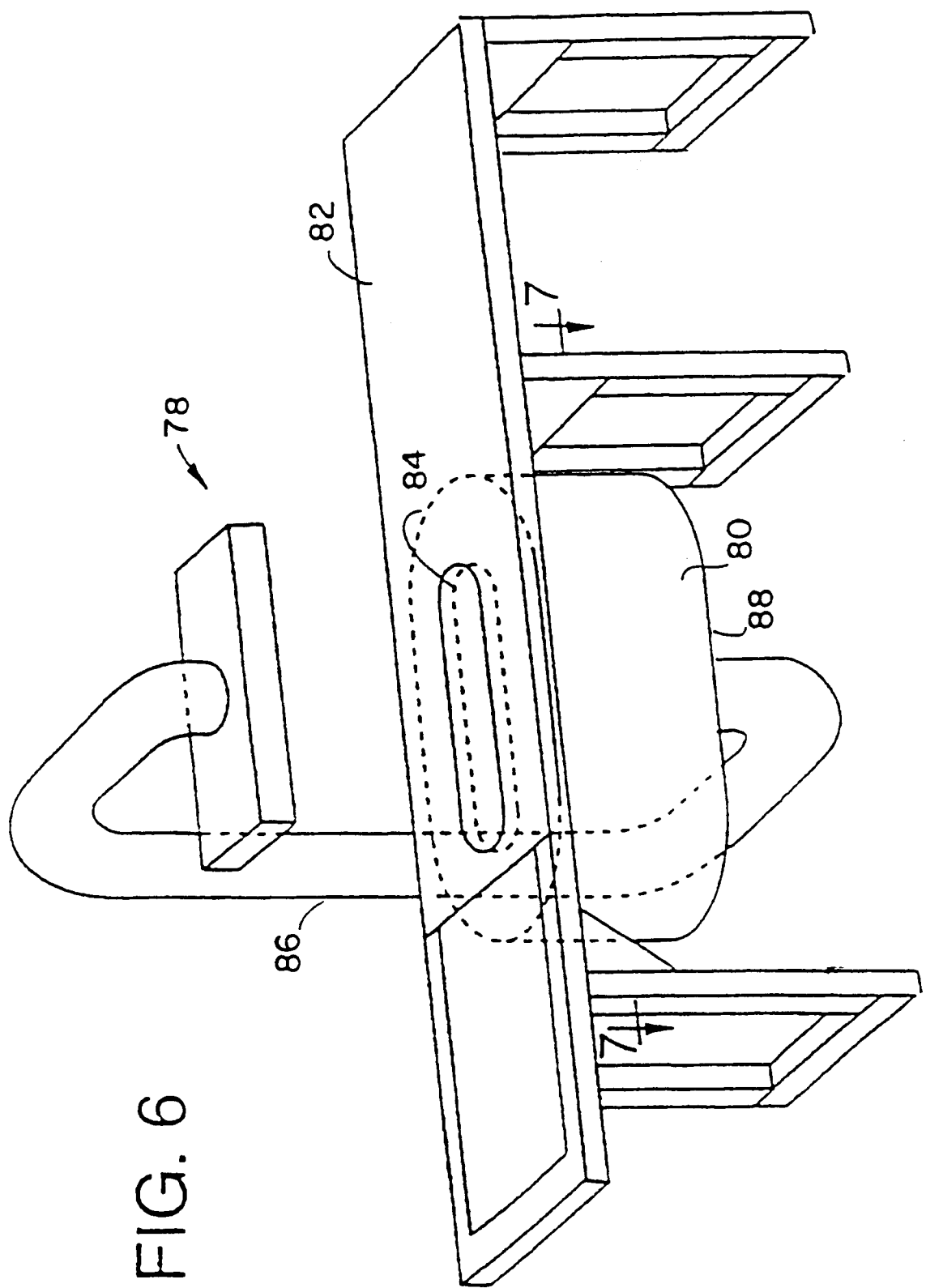
FIG. 6 is a perspective view of an alternative device using a single electromagnet for generating an oriented, unidirectional, DC magnetic field to treat a patient according to the present invention.

Referring now to FIG. 6, an alternative device 78 for generating a magnetic field for treatment according to the present invention using a single electromagnet 80 is shown. The single electromagnet 80 is positioned directly under a horizontal patient support 82 with one magnetic pole 84 facing up. A magnetic circuit 86 is connected to the bottom pole 88 and is positioned with a gap 90 in which the patient may be positioned. The magnetic circuit 86 minimizes the fringing effect of the magnetic field by providing a path for the return magnetic field.

Figure 7:
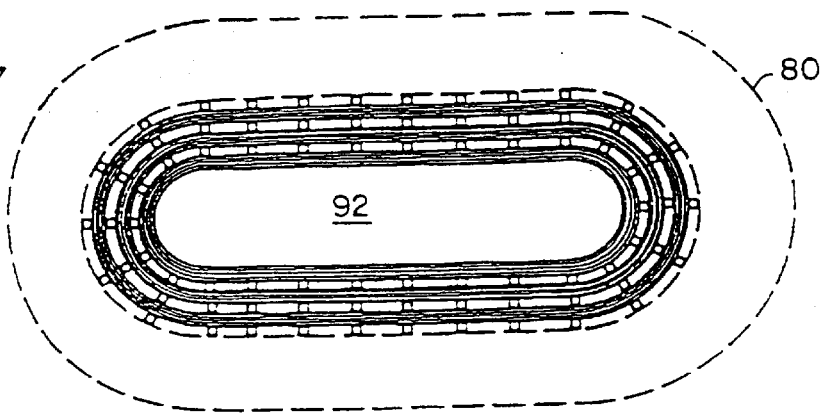
FIG. 7 is a sectional plan view of the electromagnet of FIG. 6, taken along line 7—7.

Referring now to FIG. 7, the single electromagnet 80 of the device 78 shown in FIG. 6 is wrapped on a rectangular core 92 that is 2 feet (60.96 cm) long by 3 inches (7.62 cm) wide. The electromagnet 80 comprises many windings of copper wire, as described above in reference to FIG. 3, resulting in approximately 1 foot (30.48 cm) of windings.

A Magnetic Resonance Imaging (MRI) machine may also be converted to provide a magnetic field for treatment according to the present invention. A MRI machine uses a DC magnetic field modulated with higher frequencies to determine the composition of a body within the tube. By disabling the modulation, the MRI machine can be made to provide a DC magnetic field as required by the present invention.

Figure 8:
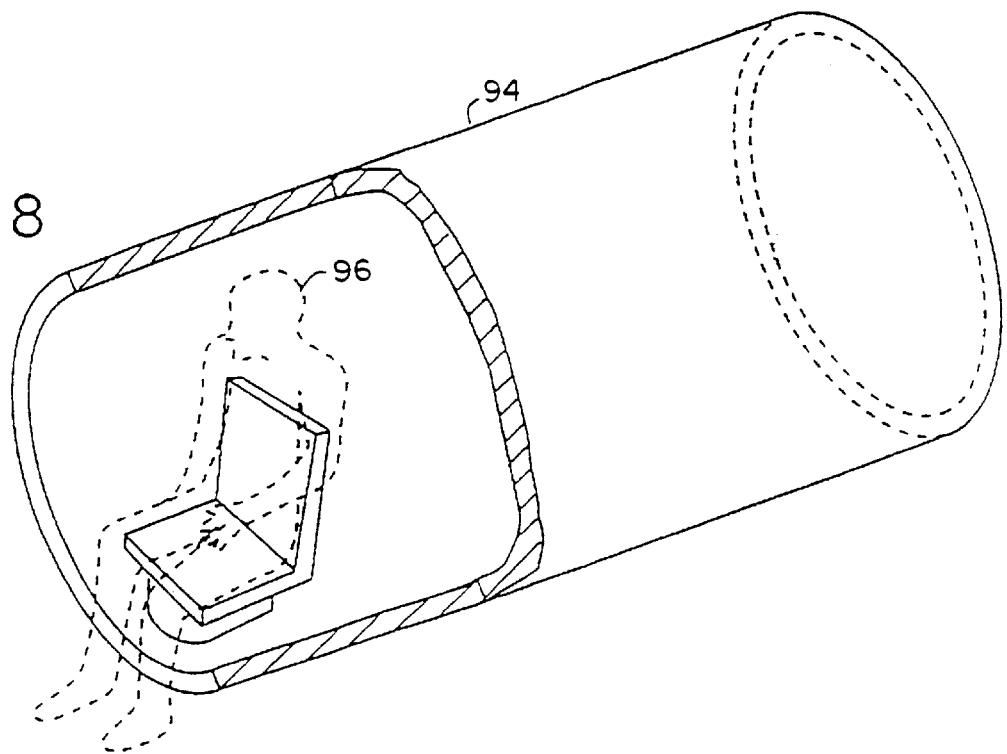
FIG. 8 is a partially cut-away perspective view of a tube-type magnetic resonance imaging machine converted to treat a patient according to the present invention.

Referring now to FIG. 8, a tube type MRI machine 94 is shown with a patient 96 sitting in a semi-reclined position. It should be noted that a relatively large diameter MRI tube is necessary to allow the patient 96 to sit in such a position. If the patient 96 is forced to lie flat, the magnetic field cannot be aligned with the ambient direction of the Earth's magnetic field, determined in the first step 20 (FIG. 1) of the method 10 of the present invention.

A converted MRI machine 94 is not ideal, however, for implementing the present invention because of the typically small diameter of the tube. Additionally, it will be recognized that even a relatively large diameter MRI tube will not allow the patient's legs to fit perpendicular to the magnetic field, thus not getting the maximum effect on the legs.

Theoretical Background

Although the precise mechanism by which the magnetic field of the present invention interacts with the body tissue of a patient are not known, the following is a description of what is believed to be occurring.

The behavior of electrons in a magnetic field is a complex phenomenon, and this description, by necessity, includes much simplification. These phenomena cannot be investigated using only classical physics, since subatomic particles obey the laws of quantum mechanics. In the Bohr model of the atom, electrons follow circular orbits around an atom's nucleus. Quantum mechanics states that it is only probable that an electron will be found in a definite region of space near the atomic nucleus, but that it is not possible to find its exact location. Proper solution can only be obtained by solving the Schrbdinger wave equation, which gives the probability of finding an electron in a given region.

Electrons in an atom have respective magnetic dipole moments based on their orbit of the atomic nucleus and on their spin. As electrons fill the orbital shells surrounding the nucleus, they are paired such that the spin of one is opposite to the other, thus mutually canceling their magnetic dipole moments. The presence of unpaired electrons results in paramagnetic and ferromagnetic properties.

In the case of atoms with valence electrons (that is, the outermost, interacting electrons) in the s shell, namely the first two columns of the periodic table, the alkali metals (including sodium, potassium) and the alkali earths (including calcium), the shape of the electron density cloud is spherical, and thus, the net effect of a magnetic field on the shape of the orbit of the electron is zero, since the orbit is symmetrical in all directions.

For valence electrons in the p or d shell, the effect of the magnetic field is to split the shell into several different levels, some of which have higher, some lower, energy states. If the shell is entirely filled (as is the case with the noble gasses, the periodic column headed by helium, and the metals of the column headed by zinc), these differences in energy level exactly cancel, leaving the atom in an energy state equivalent to one not inside a magnetic field. For partially filled electron shells, the electrons will first occupy the lower energy states, then fill the higher states. So an orbiting electron will, if possible, change the alignment of its orbit so as to be in the lowest potential energy state. This is similar to the torque exerted by a magnetic field on a current loop.

However, the angular velocity of an orbiting electron in a magnetic field is described by $$\omega_L = -\frac{e}{2m}\vec{B} \qquad (1)$$

where $\omega_L$ is the angular velocity (also called the "Larmor frequency"), e is the charge of the electron ($1.6 \times 10^{19}$ C), m is the mass of the electron ($9.1 \times 10^{-31}$) kg), and $\vec{B}$ is the magnetic field vector, in webers per square meter (1 Gauss= $10^{-4}$ W/m ). An electron experiences a frequency increase when subjected to an externally applied magnetic field. The table below represents the maximum possible frequency increase of a single electron, due to an external magnetic field.

TABLE (1)

| Field Intensity (W/m$^2$) | $10^{-4}$ | $10^{-3}$ | $10^{-2}$ | $10^{-1}$ | 1 |
|---|---|---|---|---|---|
| $\omega_L$ | $8.8 \times 10^6$ | $8.8 \times 10^7$ | $8.8 \times 10^8$ | $8.8 \times 10^9$ | $8.8 \times 10^{10}$ |
| Frequency Increase (Hz) | $1.4 \times 10^6$ | $1.4 \times 10^7$ | $1.4 \times 10^8$ | $1.4 \times 10^9$ | $1.4 \times 10^{10}$ |

The actual frequency change experienced by an electron may be smaller, especially in multi-electron atoms, depending on the orientation of the electron orbital. Sodium and potassium both have a single s shell valence electron, calcium has two. Carbon, phosphorus, oxygen, and chlorine each have at least one unpaired electron in an orbital of the p shell, which will be susceptible to the maximum frequency increase. The other electrons, having a unique orientation, may experience a frequency increase, but not to the maximum extent.

This increase in frequency apparently causes an increase in the rate of chemical reactions within a patient's body, thereby initiating and quickening the healing of damaged or weakened organs and systems.

The electromotive force (emf) acting on an electron in a magnetic field is $$\delta = -\frac{d\phi}{dt} = -A\frac{dB}{dt} \qquad (2)$$

where the Greek symbol φ (phi) represents the magnetic flux, A is the perpendicular area of the electron's orbit, B is the magnetic field, and t is time. If the orbit is not perpendicular to the magnetic field, A becomes A sin θ, where θ is the angle between the plane of the orbit and the direction of the magnetic field.

The general trend is for atoms to get larger as one moves down the periodic table, and smaller as one moves from left to right.

Applying a 0.5 w/m (5000 Gauss) change in the magnetic field over the following times results in the electromotive force acting on an electron according to the following table.

TABLE (2)

| Element\Time (s) | 1 | 10 | 100 |
|---|---|---|---|
| Hydrogen | $1.0 \times 10^{-21}$ | $100 \times 10^{-24}$ | $10 \times 10^{-24}$ |
| Carbon | $7.7 \times 10^{-21}$ | $770 \times 10^{-24}$ | $77 \times 10^{-24}$ |
| Oxygen | $5.6 \times 10^{-21}$ | $560 \times 10^{-24}$ | $56 \times 10^{-24}$ |
| Phosphorus | $15.7 \times 10^{-21}$ | $1570 \times 10^{-24}$ | $157 \times 10^{-24}$ |
| Potassium | $76 \times 10^{-21}$ | $7600 \times 10^{-24}$ | $760 \times 10^{-24}$ |
| Sodium | $51 \times 10^{-21}$ | $5100 \times 10^{-24}$ | $510 \times 10^{-24}$ |
| Chlorine | $15.7 \times 10^{-21}$ | $1570 \times 10^{-24}$ | $157 \times 10^{-24}$ |
| Calcium | $51 \times 10^{-21}$ | $5100 \times 10^{-24}$ | $510 \times 10^{-24}$ |

Obviously, the change in emf due to the introduction of a 5000 Gauss magnetic field is negligible in all elements.

Case Studies

Case study #1: A 48-year old male suffered from a glioblastoma class IV cancer, the most aggressive state of brain cancer. According to a team of cancer specialists in Toronto, Ontario, Canada, patient 1 was given a life expectancy of two months with no treatment regimen recommended due to malignancy, size, and the progressed state of the cancer growth and the extent of the lesion. Magnetic Resonance Imaging (MRI) had verified necrosis in the areas of the brain controlling motor function. Patient 1 arrived in comatose state, unable to walk or stand, with muscles exhibiting a spastic condition.

Patient 1 was treated according to the present invention by application of a 3,000 to 10,000 gauss magnetic field to the general tumor area in the brain. The magnetic field was applied for 14 hours per day for 11 days. As a result, at the end of treatment, patient 1 was able to talk and walk.

There was some concern that the improvement may have been the result of "debulking," that is, a decrease in pressure of the affected area because of a decrease in the tumor's size. The MRIs, however, indicated that the affected areas had necrosed. Thus, function would not have returned due to debulking.

Case study #2: A 31-year old female suffering from viral encephalitis, with necrosis in the right optic nerve area. Patient 2 had been diagnosed with complete right optic nerve necrosis, with the diagnosis confirmed by magnetic resonance imaging. Patient 2 had been in the hospital for two months during the acute phase.

Patient 2 was treated according to the present invention with a 3,000 to 10,000 gauss magnetic field to the affected area for two hours per day for seven days.

As a result, the patient experience a return to 60% vision, with otherwise complete recovery except for some peripheral vision.

Case study #3: A 22-year old male suffering from cancer and having undergone a partial removal of spinal cord tissue. Eight months previous, patient 3 underwent a surgical removal of Class IV glioblastoma of spinal cord from C4 to T1 area of the vertebra, leaving a small strand of neural tissue on the ventral (anterior) side.

Cancer was still present, according to a medical clinic in the Chicago area even after patient 3 had undergone radiation and chemotherapy following the surgery. Patient 3 was paralyzed from the waist down, with the exception of a sensory feeling in the right big toe, which apparently corresponded to the sole remaining neural tissue in the C4 to T1 section of the spinal cord.

Patient 3 was treated according to the present invention with a 5,000 gauss magnetic field to the C4 to T1 vertebra area for 10 to 15 hours per day for 11 days. The treatment total approximately 130 hours.

Sensory feeling increased through the last six days of treatment. Patient 3 had regained enough motor function of his lower extremities to walk behind his wheelchair, using it as a prop, pushing it ahead of him, without help.

In a follow-up examination four months later, some function that patient 3 had achieved had been lost in the intervening time. An additional 120 hours of treatment over another 11 days resulted in a similar gain in motor function and sensation that had been achieved in the first treatment series.

One year later, patient 3 reports no further cancer growth.

Case study #4: A 23-year old male suffered severe brain damage in the form of a mostly-severed Corpus Callosum and multiple brain contusions from an automobile accident eight months previous. According to X-ray reports and medical diagnosis, there was a severance of the Corpus Callosum an multiple brain contusions. He was unconscious for two months. Upon regaining his consciousness, it was found that he had no bilateral coordination of any body functions, such as eyes, arms, legs and feet. It was further discovered that he had no short term memory, no cognitive reasoning ability, no sense of smell and no sense of taste.

Patient 4 used the following six months in efforts of rehabilitation by quality physicians and physical therapists in the Los Angeles, Calif., area. During that time, he regained enough motor function to walk in a stiff-legged fashion like a wooden soldier. With concentration, he regained some use of his hands. Bilateral coordination was still lacking in the arms, eyes, and feet, as well as a lack of short term memory, and the senses of smell and taste. He was not able to read other than to recognize some basic signs such as restroom signs and the like.

Patient 4 was treated according to the present invention with a strong unidirectional magnetic field for 17 to 18 hours per day for 8 days. As a result, on the fifth day of treatment, his eyes began to coordinate and focus together. On the sixth day of treatment, he was able to read and read an entire book during treatment. On the seventh day, he read another book during treatment.

Unfortunately, due to a family emergency, patient 4 had to terminate his treatment and return to his home in Montana. However, prior to his leaving, testing and examination showed that his short term memory had been restored, his cognitive reasoning had returned, and that he could recognize smells and tastes. He could also run with coordination difficulty for a short distance.

Case study 5: A 30-year old male suffering from total paralysis, with the exception of his eyelids, due to a Pons infarct. Patient 5 had been a chiropractic student at the time of injury and had been the subject of a student partner practicing manipulation with vertebrae of the neck. He received an injury to one of the arteries in the neck which caused a blood clot to lodge in the Pons causing a Pons infarct. When he regained consciousness, it was discovered that he was totally paralyzed with the exception of the eyelids. The eyes could focus but not coordinate.

Patient 5 had been treated in many clinics throughout southern California with the hope of some recovery. The results of 8 years of treatment was the recovery of some feeling to the left half of his head and some motor function to the left half of his head. He was also able to move his left index finger.

Patient 5 was then treated according to the present invention with a unidirectional magnetic field applied to the whole head for 3 to 4 hours per day for 30 days, for a total of 120 hours of treatment.

As a result, all motor and sensory function to the right side of patient 5's head and neck was restored allowing him to hold his head up, smile, and generally use facial expressions. His swallow reflex was restored. Some motor function was restored although he could not yet walk. Most sensation to the whole body was restored. Eye coordination was restored.

During one examination, it was noticed that his skull was dislocated and was pinching his spinal cord. When his skull was held in proper alignment, he had full function of his body. He was sent to an orthopedic treatment clinic for proper fixation and alignment of his skull to spine.

Patient 5 has not recovered his speech, but it is considered likely that it will return slowly, because speech is learned. He may have to relearn to speak.

The following case studies were performed in determining the appropriate levels and effectiveness of the present invention.

Case study #6: A 55-year old female suffered a head injury in an automobile accident two years previous. She suffered of excruciating, extended headaches and gall bladder dysfunction which resulted in the gall bladder's inability to break down fats, thereby requiring a limited diet.

Patient 6 was treated according to the present invention with 3000 Gauss to her head for five days, ten hours per day for a total of fifty hours. As a result, her headaches were completely eliminated. Patient 6 was also treated according to the present invention with 3000 Gauss to her liver and gall bladder for a total of thirty hours. As a result, her digestion returned to normal.

Case study #7: A 65-year old male experienced a sub-arachnoid hemorrhage. Approximately two months later, he had the following symptoms: (1) weakness of legs and gluteus maximums muscle; (2) partial hearing loss; (3) whole-body weakness; (4) eyesight decreased from pre-stroke level; (5) constant mental fatigue; and (6) poor memory and cognitive reasoning (as an example, patient 7 could no longer add or subtract his checkbook balances.)

Patient 7 was treated according to the present invention with 3000 Gauss to his brain for 72 hours over 6 days. As a result (1) he achieved a 60 percent recovery of strength to his leg muscles and gluteus maximus; (2) his hearing returned to normal; (3) he has returned to normal activity, his muscles have continued to strengthen; (4) his eyesight has returned to normal; (5) his mental fatigue has been almost eliminated; and (6) his mental acuity has improved back to normal with excellent memory and cognitive reasoning.

Case study #8: A 66-year old male had a metastasized melanoma diagnosed approximately 11 months previous. Its original site had been the anus, but had metastasized to the lungs and lymph system, primarily around the lung area.

Patient 8 was treated according to the present invention with 2500 Gauss to the lung for 6 days, 12 hours per day, for a total of 72 hours. Patient 8 also received 12 Manaloe capsules per day, 12 Phytaloe capsules per day, and 20 grams of milk whey protein (Immunocal) per day. As a result, the cancerous lymph node in the left axial completely disappeared. Patient 8 experienced increased energy and physical performance as gauged by exercise routines. After six days of treatment, patient 8 increased the number of pushups in one workout session from 60 to 94. On radiological exam, it was determined that his main lesion in the mediastinium area of the lungs had shrunk from 5 cm to 2.5 cm in diameter.

Case study #9: A 75-year old female suffering from a progressive Alzheimer's disease for six years was unable to remember what food she had eaten at the last meal or where she was. She would ask the same question every other minute for up to an hour. Her personality was limited by her ability to express herself.

Patient 9 was treated according to the present invention with 4000 Gauss to her brain for three hours per day for four days for a total of twelve hours. As a result, patient 9 experience an improvement to her memory: she could remember some things that she had eaten at the last meal; Patient 9 no longer exhibited repetitive questioning; and her personality returned to 80 percent of normal. However, without further treatment, in time she reverted to her old condition.

Case study #10: A 53-year old female suffering from muscular dystrophy (limb girdle type) for 14 years. Patient 10 presented with all of her muscles, except her eye muscles, in a weakened state. She had not been able to raise her hands above her breast for years, could not move her legs, and had a difficult time swallowing. She also experienced sensation of coldness.

Patient 10 was treating according to the present invention with 3000 Gauss to her brain for 2.5 hours per session for 4 sessions for a total of 10 hours. As a result, patient 5 experienced: (1) increased feeling of body warmth; (2) improved stamina; (3) improved swallowing (she stopped choking); (4) improved bowel function; (5) increased dexterity; (6) less muscle soreness in her neck; (7) increased mental alertness; (8) better balance; and (9) increased muscle strength in that she was able to raise her arms over he head.

Case study #11: A 48-year old female experienced a hemorrhagic stroke on the left side of her brain resulting in paralysis of the right side of her body. As a result of occupational therapy and intensive treatment, she had recovered some sensory and motor function some fifteen months following the stroke. Nonetheless, at the start of treatment, patient 11 suffered from: (1) speech impairment; (2) facial paralysis on the right side; (3) functioning of only the deltoid and bicep muscles on the right arm; (4) limited functioning of the right leg (patient 11 could barely walk with the aide of a walker); and (5) a limited personality.

Patient 11 was treated according to the present invention with 3000 Gauss to the brain for 300 hours over a 28-day period. As a result, she experienced greatly improved sensory and motor function to both sides of the body, with substantial improvement to the right side. Her speech returned to nearly normal; her facial paralysis disappeared; improved right arm functioning (but not to fingers); she was able to walk without assistance; and her former personality returned, which pleased her family greatly.

Case study #12: A 68-year old male suffered from idiopathic neuropathy (muscular dystrophy) for 17 years. All of his muscles had reduced function. The muscles of his left leg had withered due to lack of enervation. He could only work for two hours per day due to extreme muscle fatigue. He only could walk slowly and carefully short distance with a left leg brace.

Patient 12 was treated according to the present invention with 3000 Gauss to his cerebellum for 25.5 hours. As a result, there was a return of enervation to his left leg. After only 10 hours of treatment he was able to go on a 7-mile hike in the mountains and keep up with the other hikers. He has been able to return to full-time work of approximately 12 hours per day and reports that he "feels great!" The dorsal flexion of the left foot is still weak, but the rest of his muscles are returned to a normal functioning level.

Case study #13: A 22-year old female destroyed the anterior cruciate ligament of her left knee in a tennis accident 11 years previous. She had undergone six surgeries in six years attempting to improve her range of motion and decrease her continual pain. Prior to treatment, her range motion was reduced 10 degrees in both flexion and extension.

Patient 13 was treated according to the present invention with 5000 Gauss through the cruciate ligament of her left knee for 1.5 hours. As a result, all pain in her left knee was gone and she had full range of motion. She does believe, however, that her left knee is still weaker than the right one.

Case study #14: A 73-year old female suffered from Parkinson's disease for over 6 years. Her symptoms included: (1) poor balance; (2) a general whole-body weakness, being most pronounced in her left hand; (3) constipation; (4) feeling morose; (5) inability to step backwards or sideways; (6) inability to clap her hands or raise hands over her head; and (7) having a mask face due to muscle weakness.

Patient 14 was treated according to the present invention with 4000 Gauss through her brain for 97.5 hours over a 14-day period. As a result her balance is now good. Her overall strength is good and her left hand is back to normal strength. Her constipation has been eliminated. She has a good attitude. She can now walk backwards and sideways and can even dance. She can clap her hands and raise them over her head. Her mask face is gone; it's replaced with smiles.

Case study #15: A 91-year old female suffered from congestive hear failure. She could not walk anywhere without experiencing shortness of breath and panting.

Patient 15 was treated according to the present invention for two weeks. As a result, she is now able to walk for two miles at a time.

Case study #16: A 68-year old male suffered from high blood pressure: 190/105.

Patient 16 was treated according to the present invention for approximately 50 hours over a 6 day period. As a result, his blood pressure dropped to 138/78.

Case study #17: A 62-year old male had an atrial node that was misfiring.

Patient 17 was treated according to the present invention for 12 hours in one session. As a result, his heart ceased its atrial fibrillation.

The case studies tend to show that the method of treatment according to the present invention is beneficial for general tissue regeneration, including muscles and the central nervous system. Other case studies are pending, with research being done on brain conditions such as cerebral palsy, autism, and attention deficit hyperactivity disorder.

The terms and expressions which have been employed in the foregoing specification are used therein as terms of description and not of limitation, and there is no intention, in the use of such terms and expressions, of excluding equivalents of the features shown and described or portions thereof, it being recognized the scope of the invention is defined and limited only by the claims which follow.

What is claimed is:

1. A method of treating a portion of a patient's body, where the patient lives within an environmental magnetic field, comprising the steps of:
   (a) determining a direction of the environmental magnetic field with respect to the portion of the patient's body during cell division;
   (b) placing the portion of the patient within a treating magnetic field, such that said treating magnetic field is oriented within 90 degrees of said direction determined in step (a), where said treating magnetic field is DC and has an intensity of at least 500 gauss.

2. The method of claim 1, wherein the placing step further comprises the step of orienting said treating magnetic field within 45 degrees of said direction determined in step (a).

3. The method of claim 1, wherein the placing step further comprises the step of orienting said treating magnetic field within 30 degrees of said direction determined in step (a).

4. The method of claim 1, wherein the determining step further is characterized by determining a direction of he Earth's magnetic field with respect to the portion of he patient's body during the patient's first two hours of sleep.

5. The method of claim 4, wherein the placing step further comprises the step of orienting said treating magnetic field within 45 degrees of said direction determined in step (a).

6. The method of claim 4, wherein the placing step further comprises the step of orienting said treating magnetic field within 30 degrees of said direction determined in step (a).

7. The method of claim 4, wherein the determining step further is characterized by observing the patient's body during the patient's first two hours of sleep.

8. A method according to claim 1, wherein the treating magnetic field is produced by at least one electromagnet.

9. A method according to claim 8, wherein the electromagnet is cooled with a fluid coolant selected from the group consisting of air, water, oil, liquid hydrogen, liquid helium, liquid nitrogen, liquid air and liquid oxygen.

10. A method according to claim 1, wherein return lines of the treating magnetic field do not pass through any portion of the patient's body.

11. A method according to claim 1, wherein the portion of the patient's body treated is a brain.

12. A method according to claim 1, wherein the portion of the patient's body treated is an eye and its associated optic nerve.

13. A method according to claim 1, wherein the portion of the patient's body treated is a spine.

14. A method according to claim 1, wherein the portion of the patient's body treated is a neck.

15. A method according to claim 1, wherein the portion of the patient's body treated is a head.

16. A method according to claim 1, wherein the portion of the patient's body treated is a lung.

17. A method according to claim 1, wherein the portion of the patient's body treated is a knee.

18. A method according to claim 1, wherein the portion of the patient's body treated is a heart.

* * * * *